United States Patent
Knudson et al.

(10) Patent No.: US 6,860,851 B2
(45) Date of Patent: Mar. 1, 2005

(54) VULNERABLE PLAQUE DIAGNOSIS AND TREATMENT

(75) Inventors: Mark B. Knudson, Shoreview, MN (US); Timothy R. Conrad, Eden Prairie, MN (US); Katherine S. Tweden, Mahtomedi, MN (US)

(73) Assignee: EnteroMedics Inc., St. Paul, MN (US)

( * ) Notice: Subject to any disclaimer, the term of this patent is extended or adjusted under 35 U.S.C. 154(b) by 95 days.

(21) Appl. No.: 10/306,872

(22) Filed: Nov. 27, 2002

(65) Prior Publication Data

US 2004/0102686 A1 May 27, 2004

(51) Int. Cl.[7] .................................................. A61B 5/00
(52) U.S. Cl. ...................................... 600/309; 600/549
(58) Field of Search ................................ 600/322, 309, 600/549, 361, 341, 342

(56) References Cited

U.S. PATENT DOCUMENTS 6,541,265 B2 * 4/2003 Leeuwenburgh ............. 436/86
6,712,771 B2 * 3/2004 Haddock et al. ............ 600/549
2002/0115931 A1 * 8/2002 Strauss et al. .............. 600/420
2004/0073132 A1 * 4/2004 Maahs et al. ............... 600/549

* cited by examiner

Primary Examiner—Eric F. Winakur
Assistant Examiner—Matthew Kremer
(74) Attorney, Agent, or Firm—Merchant & Gould P.C.

(57) ABSTRACT

Vulnerable plaque is identified through a diagnostic method by identifying pathologic markers such as C-reactive proteins or pH change generated by the pathologic site. First and second detectors are advanced through a blood vessel with each of the detectors selected to detect the pathological marker. The detectors are spaced apart while seeking the marker. Differential concentration of the pathological marker as measured by the first and second detectors indicates a presence of the pathological site in proximity to at least one of the detectors.

8 Claims, 1 Drawing Sheet

VULNERABLE PLAQUE DIAGNOSIS AND TREATMENT

BACKGROUND OF THE INVENTION

1. Field of the Invention

This invention pertains to a method and apparatus for diagnosis and treatment of pathologic sites within a blood vessel. More particularly, this invention pertains to such method and apparatus for diagnosis and treatment of vulnerable plaque.

2. Description of the Prior Art

The formation of plaque within blood vessels has long been recognized as a serious disease requiring medical intervention. Commonly, the focus of medical intervention has been on so called "stenotic" plaque. Stenotic plaque is commonly characterized as a stable plaque in the form of a thick fibrous cap. The plaque may occlude a blood vessel by 50% or more.

At about 50% stenosis (i.e., 50% occlusion of a blood vessel,) such plaque is symptomatic in that the patient experiences chest pain (referred to as angina). Treatment of such plaque typically occurs when the blood vessel is occluded by 70% or more.

The identification of stenotic plaque is readily determined and visualized through standard procedures such as IVUS (intravascular ultrasound), angiography or fluoroscopy. Once the location of a stenotic plaque is identified, the plaque may be treated through any one of a number of treatment modalities including angioplasty, placement of a stent, or coronary bypass surgery. Recently, the introduction of drug-eluting stents have been used for the treatment of such plaque.

Unfortunately, an additional category of plaque has historically evaded detection and treatment. This second category of plaque is referred to as vulnerable plaque which appears to be caused by an inflammatory response to unacceptable levels of pathologic compounds in the vessel wall—such materials include cholesterol and other lipids and the like.

Vulnerable plaque is believed to be responsible for as much as 85% of heart attacks. Vulnerable plaque has been defined as a plaque which is often not stenotic and has the likelihood of becoming disruptive and forming a thrombogenic focus.

Unlike stable plaque, vulnerable plaque is commonly associated with a pool of lipid material separated from a blood vessel by a thin fibrous cap. Typically, vulnerable plaque does not protrude into the blood vessel by more than 50%. However, when the thin fibrous cap exposes the lipid through either rupture or erosion, the lipid can instigate rapid thrombus formation within the blood vessel leading to infarction or stroke. When the plaque ruptures there is contact between the blood, the lipid core and other plaque compounds that appears to instigate the majority of coronary thrombi.

Since the vulnerable plaque does not protrude as significantly within the blood vessel as stenotic plaque, such vulnerable plaque is often not identifiable through traditional visualization technique such as angiography. Also, a patient typically has no symptoms prior to heart attack. Therefore, vulnerable plaque presents a significant diagnostic problem. A significant diagnostic issue is presented in attempting to determine who is prone to vulnerable plaque, identifying the plaques and localizing plaques that are of high vulnerability and capable of causing a catastrophic event.

Certain primary disease markers are believed to help identify the existence of vulnerable plaque in a patient's vasculature. For example, C-reactive protein (CRP) is a promising primary marker for vulnerable plaque.

Elevated cholesterol levels, specifically LDL levels, have long been one of the key risk factors used to identify a risk for coronary artery disease. However, recent research has centered on the validity of C-reactive protein as a key heart disease marker.

CRP is a protein most commonly associated with inflammation. CRP levels rise as the amount of inflammation in the body rises. CRP has been shown to be localized at the point of inflammation and to be systemic and disbursed throughout the body. CRP is of interest to clinicians and so may be a primary marker for predicting the existence of vulnerable plaque, which is an inflammatory response.

In addition to CRP, other primary markers are T-wave alternans and calcium deposition determined by radiographic temography or MRI. CRP is a biomarker produced in the liver in response to multiple inflammatory, infectious and immunological challenges. It is also believed that temperature differentials are a possible way to localize vulnerable plaques. Other techniques for identifying plaque include optical coherence tomography (OCT) and thermography. OCT measures a difference in an index of refraction between fibrous tissue and macrophage-laden tissue. OCT is limited by depth of penetration (2 mm) and clinician interpretation of the image. Thermography relies on temperature differentials of 0.1–0.2° C. higher than non-diseased vasculature as a predictor of vulnerable plaque. The thermistors need good contact with the lesion which leads to concerns that the device itself may cause plaque to rupture.

While CRP is a promising marker, it is previously believed to be used only as a general screening technique since it is typically identified as a systemic response not adequate to localize and identify a specific plaque.

Another example of a marker is a change in acidity (i.e., pH) of the blood near a vulnerable plaque. The pH of the inflamed vulnerable plaque can be as low as 6.3 versus a normal blood pH of 7.4. This change in pH affects the local environment as well (e.g., changes in blood pH permitting indirect detection of pH in the inflammatory site).

It is an object of the present invention to provide a method and apparatus for diagnosing and localizing vulnerable plaque or other pathologic site.

SUMMARY OF THE INVENTION

According to a preferred embodiment at the present invention, a diagnostic method and apparatus are disclosed for identifying a pathologic site in a blood vessel of a patient's vasculature. The pathologic site is characterized by a generation of a pathologic marker. The method includes advancing first and second detectors into the vasculature with each of the first and second detectors selected to detect the marker. The first and second detectors are spaced apart while the detectors are seeking detection of the marker. At least one of the detectors is advanced through the vessel with a concentration differential between the first and second detectors indicating a presence of the pathological site in proximity to at least one of the detectors.

DESCRIPTION OF THE PREFERRED EMBODIMENT

Referring now to the several drawing figures, in which identical elements are numbered identically throughout, a description of a preferred embodiment of the present invention will now be provided.

Figure 1:
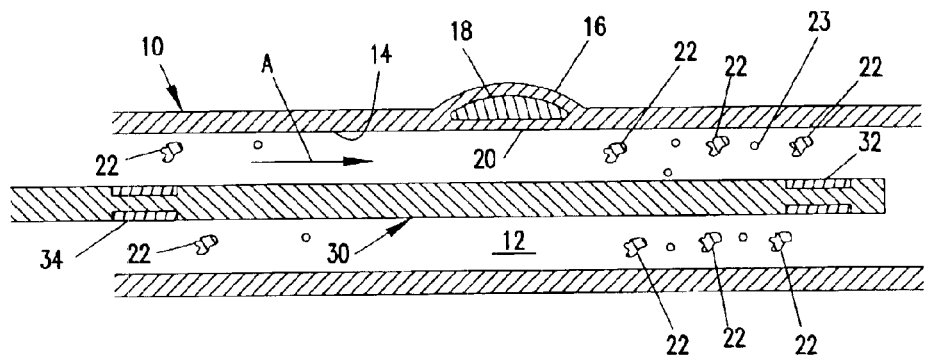
FIG. 1 is a side-sectional schematic view of a blood vessel having a vulnerable plaque as a pathologic site and with an apparatus positioned within the blood vessel to localize and identify the pathologic site.

In FIG. 1, a blood vessel 10 (such as a coronary artery) is shown having a lumen 12 defined by an endothelium layer 14 of the blood vessel 10. A pathological site 16 exists within the wall of the blood vessel 10. In the embodiment shown, the pathological site 16 is a vulnerable plaque site characterized by a lipid pool 18 within the wall of the blood vessel and covered by thin fibrous cap 20.

The blood vessel 10 contains a flow of blood in the direction of arrow A. Entrained within the blood flow are numerous pathological markers and other components of the blood flow. These pathological markers will include C-reactive proteins illustrated schematically as elements 22 (and shown greatly enlarged in the figures for ease of illustration). Other such markers (evaluated independently or concurrently with C-reactive protein) include excess hydrogen ions 23 (again, shown greatly exaggerated in size) indicating a reduced pH. In the case of such C-reactive proteins 22, substantial quantities can be generated by the liver in response to inflammation throughout the body and may exist in a relatively high concentration (for example, measured in milligrams per liter) within the blood.

In addition to C-reactive proteins being produced by the liver, such C-reactive proteins 22 are also produced at the site of an inflammation such as at the pathologic site 16. Accordingly, FIG. 1 schematically shows additional C-reactive proteins 22 on a distal (downstream) side of the pathologic site 16 in a higher concentration than on a proximal side (upstream) of the pathologic site 16. The same is true for excess hydrogen ions 23 produced at the inflammatory site.

The number of additional C-reactor proteins 22 shown on the distal side is greatly exaggerated in FIG. 1. For example, while the a systemic concentration of C-reactive proteins may be measured in milligrams per liter as previously mentioned, the additional contribution of C-reactive proteins 22 from the pathologic site directly 16 may be measured as an additional micrograms per liter. This relatively small additional contribution directly from the pathological site 16 makes detection and localization of the pathological site 16 complicated.

In order to detect and localize the pathological site 16, an apparatus 30 is provided in the form of an elongated flexible catheter sized to be advanced through the blood vessel 10. The catheter includes a first detector 32 and a second detector 34 contained on the catheter 30. The detector 32, 34 are spaced apart with detector 32 being distal to proximal detector 34. The catheter 30 may have an internal lumen (not shown) to advance the catheter over a guide wire (not shown) as is common in conventional catheter and guide wire systems.

The detectors 32, 34 are selected to detect and measure pathological markers emitted or generated by the pathological site 16. In the preferred embodiment, the detectors 32, 34 are selected to detect and measure C-reactive proteins 22 and/or hydrogen ions (pH). While the detection of C-reactive proteins and/or pH may be preferred, the detection of other markers generated by the pathological site may be utilized such as increased temperature of an inflammation site, or the emission of other markers from the pathologic site. Other markers of vulnerable plaque that may be useful for diagnostic purposes include inflammatory cytokines and the similar substances such as TNF alpha (tumor necrosis factor), IL-1 (interleukin 1), MCP-1 (monocyte chemoattractant protein-1), and NO (nitric oxide).

The detectors 32, 34 may be any one of a variety of detectors. These may include electro-chemical detectors, temperature sensors, photosensitive detectors, spectrometry detectors, or antigen-antibody reactants, which react in response to the presence of a specific protein and with the reaction being detected and measured by the detectors 32, 34. The detectors 32, 34 may be connected to a controller (not shown) for analyzing signals from the detectors 32, 34 and outputting an analysis to an operator such as a cardiologist attempting to identify and localize the pathologic site 16.

The apparatus as described, the apparatus 30 may be advanced into the vasculature. While being advanced through the vasculature in the blood vessel 10, the detectors 32, 34 are providing an output to the operator indicating concentration of C-reactive protein 22 or hydrogen ion 23 (pH) and specifically providing an indication of a concentration differential of C-reactive protein or pH between the detectors 32, 34.

As the detector 32 is advanced past the pathologic site 16, the increased concentration of C-reactive protein 22 distal to the pathologic site 16 is noted by detector 32 and compared to the lesser concentration of C-reactive protein or pH on a proximal side of pathological site as measured by detector 34. The existence of a differential concentration measured between detectors 32, 34 provides an indication to the operator that the pathogical site 16 is in close proximity to at least one of the detectors 32, 34. After such initial observation, the operator may retract the apparatus 30 until the differential is negligible indicating a precise location of the pathologic site. The detectors 32, 34 may be radiopaque or additional radiopaque markers (not shown) may be provided on the catheter 30, so precise visualization of the location of the catheter 30 can be noted through fluoroscopy.

In addition to the method described, the second and first detectors 32, 34 need not be on the same catheter. For example detector 34 may be positioned in any blood vessel in the body to provide an indication of the measurement of the systemic level of C-reactive protein or pH in the body. A separate catheter having a lone first detector 32 can be advanced through the blood vessel 10 to provide an indication of increased concentration of C-reactive protein 22 or pH distal to the pathologic site 16. In this embodiment, the detectors 32, 34 can be placed in different vessels of the patient's vasculature. Also, detector 34 may be outside of the body with blood delivered to it while detector 32 is advanced through vessel 10.

Figure 2:
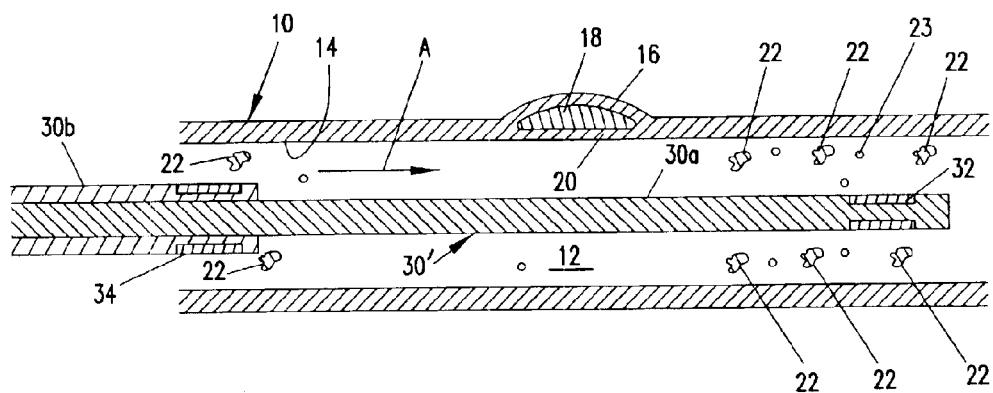
FIG. 2 is a view of FIG. 1 showing a second embodiment of the apparatus of the present invention where the apparatus includes two telescoping components each containing detectors for a pathologic marker.
Figure 3:
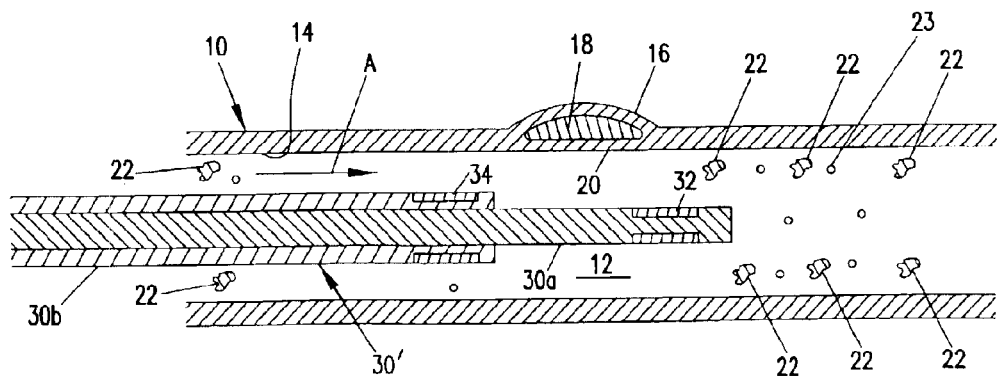
FIG. 3 is a view of FIG. 2 with the apparatus retracted to draw together and focus upon the pathologic site.

FIGS. 2 and 3 illustrate an alternative embodiment of the apparatus 30 with the alternative embodiment indicated by the apparatus 30'. The apparatus 30' includes two catheters 30a and 30b with catheter 30a slidable within catheter 30b. A distal end of catheter 30a is provided with the first detector 32. A distal end of catheter 30b is provided with the second detector 34. The detectors 32, 34 are maintained spaced apart as the entire apparatus 30' is advanced through the blood vessel until detector 32 is noted to be distal to a pathologic site as indicated by a concentration differential in C-reactive protein or pH measured between detectors 32 and 34. At the point of the measurement of the concentration differential, the spacing between the detectors 32, 34 may be narrowed by retracting inner catheter 30a relative to outer catheter 30b as illustrated in FIG. 3 to more accurately focus on the precise location of the pathologic site 16 within the blood vessel 10.

As an additional alternative, a first detector can be placed in or near the coronary sinus or other coronary vein with a second detector remotely placed (e.g., in the inferior vena cava) to isolate a marker source to the heart.

In the foregoing detailed description of the present invention, it has been shown how the objects of the invention have been attained in a preferred embodiment. Modifications and equivalents of the disclosed concepts are intended to be included within the scope of the claims which are appended hereto.

What is claimed is:

1. A diagnostic method for identifying a pathologic site in a blood vessel, of a patient's vasculature wherein said pathologic site is characterized by a generation of a pathologic marker, said method comprising:

advancing a first detector and a second detector into said vasculature with each of said first and second detectors selected to detect an intensity of said marker, said detectors being arranged to avoid contact with a wall of the vasculature;

spacing said first and second detectors apart while said detectors are seeking detection of said marker;

advancing at least one of said detectors through said vessel with each of said detectors measuring an intensity of said marker at a location in said vasculature of each of said detectors; and comparing an intensity of said marker as measured by each of said detectors and noting an increase in intensity of said marker as measured by said at least one of said detectors relative to an intensity of said marker as measured by the other of said detectors;

wherein a differential of intensity of said marker between said first and second detectors indicates a presence of said pathologic site in proximity to said at least one of the detectors and with said differential compensating for a systemic presence of said marker.

2. A method according to claim 1 comprising narrowing a spacing between said first and second detectors after said indication of said presence of said pathologic site to more narrowly focus on said pathologic site.

3. A method according to claim 1 wherein said pathologic site is a vulnerable plaque.

4. A method according to claim 1 wherein said pathologic marker is a C-reactive protein.

5. A method according to claim 1 wherein said pathologic marker is a hydrogen ion concentration (pH).

6. A method according to claim 1 wherein said pathologic marker is an increase in temperature.

7. A method according to claim 1 wherein said pathologic marker is a localized inflammation marker.

8. A method according to claim 1 wherein each of said first and second detectors is placed in said vessel.

* * * * *